(12) United States Patent
Richardson et al.

(10) Patent No.: US 6,207,190 B1
(45) Date of Patent: Mar. 27, 2001

(54) DOSAGE FORMS FOR THE TREATMENT OF THE CHRONIC GLAUCOMAS

(75) Inventors: Kenneth T. Richardson, Anchorage, AK (US); Don C. Pearson, Lakewood, WA (US)

(73) Assignee: ChronoRX, LLC, Anchorage, AK (US)

( * ) Notice: Subject to any disclaimer, the term of this patent is extended or adjusted under 35 U.S.C. 154(b) by 0 days.

(21) Appl. No.: 09/372,362

(22) Filed: Aug. 11, 1999

Related U.S. Application Data

(60) Provisional application No. 60/096,658, filed on Aug. 13, 1998.

(51) Int. Cl.$^7$ ................. A61K 9/24; A61K 9/22
(52) U.S. Cl. ........................ 424/472; 424/468
(58) Field of Search .................. 424/472, 468, 424/470, 451, 455, 489, 464

(56) References Cited

U.S. PATENT DOCUMENTS 5,962,030 * 10/1999 Fine .................................. 424/646

* cited by examiner

Primary Examiner—James M. Spear
(74) Attorney, Agent, or Firm—Townsend and Townsend and Crew LLP

(57) ABSTRACT

Four interdependent functional groups of biofactors and biomolecules are identified and formulations are defined which are comprised of their members. The active agents are demonstrated to be complementary in their physiological functions especially as these relate to endothelial biochemistry and physiology, hyperinsulinemia and, ultimately, to vascular health. The active components of the invention are selected for inclusion in precise combinations that reduce a variety of risks of vasculopathy in addition to reducing intraocular pressure. Widespread systemic improvement associated with local, optic nerve betterment of vascular health, reduces the risk of optic nerve atrophy with its accompanying visual field loss and potential blindness. The reduction of this maximizes the potential clinical therapeutic success of current medical, IOP-lowering, anti-glaucoma mediations.

56 Claims, No Drawings

DOSAGE FORMS FOR THE TREATMENT OF THE CHRONIC GLAUCOMAS

CROSS REFERENCE TO RELATED APPLICATION

This application is related to United States Provisional Patent Application No. 60/096,658, filed Aug. 13, 1998, and claims all benefits legally available therefrom. Provisional Patent Application No. 60/096,658 is hereby incorporated by reference for all purposes capable of being served thereby.

BACKGROUND OF THE INVENTION

1. Field of the Invention

This invention is in the field of pharmacology, and relates specifically to the pharmacological treatment of the chronic glaucomas of the eye.

2. Description of the Prior Art

Pertinent Anatomy of the Eye

The eye is a closed, fluid-filled environment divided into two segments separated by the crystalline lens. The anterior segment is bordered anteriorly by the arching, clear cornea and posteriorly by the anterior surface of the lens and the iris. The posterior segment is bordered in the front by the back surface of the lens and iris and posteriorly by the concave surface of the retinal lining of the globe. The only significant opening in this otherwise closed globe is through the retina in the distal back; the exit point of approximately 1 million bundled axonal nerves gathered from all points of the retina carrying their electrically digitized images for manipulation and display by the brain—our impression of this electrical activity is called vision. This opening for the bundled coaxial cable of nerves is called the optic nerve head and represents the weakest point in an otherwise very strong, inelastic globe. A locally dense, layered network of blood vessels supplies the optic nerve head and its health is almost totally dependent upon the oxygen delivered to it by this labyrinth of small vessels. These fine vessels are derived, in the main, from the short posterior ciliary arteries that arise from the ophthalmic artery. This particular vascular source for the eye is important when consideration is given to vascular reactions to vasoconstrictors and vasodilators such as endothelin-1 and nitric oxide (vide infra).

At the peripheral circumference of the posterior surface of the iris is a fringe of secretory cells (ciliary processes) which secrete a thin, watery fluid (aqueous fluid) at a relatively constant, though variable rate. This fluid passes through an intervening meshwork (trabecular meshwork) and then exits the eye through tiny openings into a collection channel that circles the interior periphery of the cornea concentric with the outer edge of the anterior iris (Schlemm's canal). The flow of aqueous fluid, therefore, originates in the periphery of the posterior chamber, washes forward around the crystalline lens through the pupil and exits through Schlemm's canal in the periphery of the anterior chamber.

Pertinent Physiology of the Eye

The eye is maintained in a homeostatic shape by a relatively stable intraocular pressure (IOP) which varies within a reasonably narrow range. This is true so long as the production of aqueous fluid by the ciliary processes remains equal to its exit through Schlemm's canal. However, should aqueous production outstrip aqueous outflow, the IOP increases. Because the eye is a closed, fluid-filled, minimally expansile organ, any hydraulic pressure increase in one part of the eye is transmitted equally throughout the eye.

So long as the availability of oxygen from the posterior ciliary arteries and the small optic nerve head arterioles remains adequate, the nerve head itself can tolerate relatively high levels of IOP. However, it is perhaps intuitively obvious that the ability of arterially-delivered oxygen to move efficiently from the red blood cells of terminal arterioles, through the arteriolar wall and into the oxygen-dependent tissues of the optic nerve head, is at least partially dependent upon the difference between the intravascular oxygen pressure and the extravascular pressure countering its diffusion. Thus, if the intraocular pressure of the globe which compresses the outside of the arterioles is higher than the oxygen diffusion pressure driving oxygen through the arteriole into the surrounding tissues, decreasing amounts of oxygen will reach the optic nerve head and nerve disability will result. Over a variable period of time this chronic, local vascular disability results in atrophy, progressive functional death of the nerve, visual field defects and blindness.

Similarly, if the vessels which carry blood to the nerve head are unable to provide sufficient volumes of blood, and thus oxygen, to the optic nerve or have structural barriers to oxygen diffusion, then even in an environment of normal or "low" intraocular or extravascular pressure (<21 mm Hg.), local tissues will be oxygen deprived and optic nerve dysfunction or atrophy will follow. These arteriolar deficiencies may occur because of vasoconstriction secondary to generalized or localized microvascular dysregulation, or in conjunction with arteriolar muscular hypertrophy (perhaps as a result of chronic spasm), atherosclerotic luminal reduction, changes in the viscosity or laminar flow patterns of the arterial blood, or in either essential or iatrogenic systemic hypotension. Interestingly, there is significant evidence that "low" or normotensive glaucoma patients do indeed have reduced optic nerve head blood flow Clearly if the intraocular pressure is elevated and the vascular ability to provide sufficient volumes of blood is compromised, the danger of optic nerve head failure is greatly increased.

Chronic Glaucoma—The Disease

Glaucoma in various guises affects a large segment of the public. It is estimated that 2% to 2.5% of the population over the age of 40 has chronic open angle glaucoma (COAG), sometimes, synonymously, referred to as Primary Open Angle Glaucoma (POAG). In this disease, there is no major structural obstruction to aqueous access to the outflow trabeculum, but there is increased resistance to aqueous transit through the trabeculum to Schlemm's canal. This is the most common form of glaucoma.

Smaller but additive segments of the population suffer from other types of chronic glaucoma: pigmentary glaucoma, angle recession glaucoma, pseudoexfoliative glaucoma and combined (mixed) mechanism glaucoma.

Although, as noted, there are several forms of the disease, all incorporate a limited number of common features, the most disastrous of which is an ultimate failure of the optic nerve leading to complete blindness. Except for some less common varieties of glaucoma, this failure usually involves asymptomatic, slowly progressive visual field loss over a very long period of years and, as a result, the patient is frequently unaware of the disease. All too often the diagnosis is made after much damage to the optic nerve has occurred and some irreversible loss of vision has taken place.

Normal IOP is given as 18 mm. Hg. Elevated IOP is classically defined as pressure over 21 to 24 mm. Hg.

Because optic nerve damage is known to occur in patients with chronically elevated or, less frequently, acutely elevated IOP, present treatment methods concentrate on reducing this easy-to-measure, objective clinical finding by the application of a variety of modalities: topical eyedrops, oral medications, intravenous medications, surgical procedures, laser phototherapy, etc. While each of these treatment approaches may function differently, they are all focused upon the reduction of pressure inside the eye and rely upon this pressure fall to prevent optic nerve damage. In some cases the therapy attempts to reduce the production of aqueous fluid by the ciliary processes, in other cases therapy attempts to increase the outflow of aqueous fluid through Schlemm's canal.

For some patients this approach is adequate and effective. However, the effectiveness of each of these treatments has a place on a treatment continuum which runs from total ineffectiveness and progressive optic atrophy and eventual blindness, to an arrest of the disease, complete cessation or prevention of further optic nerve failure and preservation of vision.

This treatment solution, however, is complicated by two facts:

a. Some patients develop progressive and seemingly irreversible optic nerve failure and visual loss in the face of normal IOP or lower than normal IOP (sometimes very much lower). These states are referred to as "normotensive glaucoma" or "low tension glaucoma".

b. Although optic nerve failure does in fact occur in patients with elevated IOP, not everyone who has IOP elevation develops optic nerve failure; in fact, most patients with higher than normal IOP do not develop optic nerve failure or visual field loss and by definition, do not suffer from glaucoma. In spite of this, many of them receive pressure-lowering medications as treatment for their "glaucoma".

Clearly, factors other than IOP level influence the clinical outcome for a large group of individuals. Currently attention is focusing upon a primary alternative: hypovascularity of the optic nerve head and loss of the vascular integrity of the optic nerve resulting in glial collapse, ganglion cell apoptosis and progressive neural atrophy with visual loss. Unfortunately, local optic nerve vascular inadequacy in the face of low IOP ("low tension" glaucoma) may result in clinical results just as damaging as those which appear in the presence of "high tension" glaucoma. Conversely, a recognizably large majority of patients with adequate optic nerve vascular integrity, even in the face of an elevated IOP, do not have progressive optic nerve damage.

A second potential variable, which may influence the clinical outcome, is hypoxic interference with retrograde axoplasmic flow within the neural axons from retinal ganglion cells to the occipital cortex. The variable ability of these axonal fibrils to continue adequate axoplasmic flow in the face of reduced oxygen availability also helps explain the variable survivability of the nerve head independent of IOP levels. It also highlights an additional functional activity of the optic nerve that is potentially sensitive to local oxygen saturation levels.

Ocular Microvascular Regulation

A balanced biochemistry of nitric oxide (NO) and endothelin-1 (ET-1) mediate local ocular blood flow and many facets of systemic vascular autoregulation.

NO is a highly soluble gas formed within endothelial cells by the action of the constitutive enzyme nitric oxide synthetase (eNOS). NO activates guanylate cyclase and increases guanosine monophosphate (cGMP) within the vascular musculature. cGMP produces relaxation and dilatation of the vessel. NO is the most powerful vascular dilator known, excepting histamine. It also may have powerful, less vascular specific and more generalized smooth muscle relaxing abilities; in this regard it would participate in the relaxation of the contractile trabecular elements of the eye and increase of aqueous outflow. An increase of aqueous outflow results in a decrease in IOP. However, levels of NO in the trabecular region of eyes of glaucoma patients are lower than in the eyes of non-glaucoma patients; this may be the effect of an inappropriate variation in the promoter region of the eNOS gene which has been found in glaucoma patients. Additionally, aging and atherosclerosis of the vascular endothelium reduce the latter's ability to produce NO because of reduced local levels of eNOS.

ET-1 is also formed within and secreted by endothelial cells. ET-1 reacts with local receptors on smooth muscle cells to produce a powerful and long-lasting vasoconstriction. ET-1 is particularly released by aged or unhealthy endothelial cells, e.g., in the presence of atherosclerosis or in the presence of locally-bound, collections of endothelial leukocytes or platelets, etc. The smooth muscle contraction produced by ET-1 strongly opposes the relaxation properties of NO and, as a result, trabecular contraction is stimulated, resistance to aqueous outflow is increased and IOP increases. At the same time this pressure increase is occurring, vasoconstriction of the small vessels of the optic nerve occurs, local hypoxia ensues and a course is set for optic nerve atrophy. Aqueous levels of ET-1 are elevated in glaucomatous eyes. Induced elevations of aqueous ET-1 levels produce optic nerve collapse.

This balance between NO and ET-1 mediates the autoregulation of blood flow within the optic nerve and the peripheral circulation. Interestingly, the vascular reactivity of the peripheral circulation to ET-1 is much more pronounced in glaucoma patients than in non-glaucomatous subjects and is particularly elevated in low tension glaucoma patients.

Exposure of patients to vasodilating stimuli or to calcium channel blockers has resulted in an improvement of the glaucomatous visual field. This is understandable since vascular endothelial production of ET-1 is dependent upon cytosolic calcium influx via transmembrane calcium channels. Calcium channel blockade reduces this calcium influx and reduces the production of ET-1. A reduction of IOP has been observed as a side effect in glaucoma patients using calcium channel blockers for systemic hypertension. However, prescribing therapeutic doses of calcium channel blockers to non-hypertensive glaucoma patients subjects the optic nerve to a risk of hypoxia secondary to iatrogenic hypotension and produces gross, unstable perturbations of cellular calcium fluxes (vide infra, Calcium Wave Modulation).

Ocular Vascular Disease

Ocular vascular diseases can exist in a variety of forms and result in a variety of pathological clinical conditions. All are associated with a reduction of oxygen delivery to surrounding, dependent tissues. In the optic nerve there are two tissues particularly vulnerable to hypoxia:

a. The microglial ganglion cells which are necessary for the functional health of the retinal axons traversing the optic disc; and b. the transiting axonic neurons themselves and their dependency upon a healthy oxygen environment and adequate axoplasmic flow.

A reduction in optic nerve oxygen delivery may follow acute or chronic, segmental or widespread, vascular spasm or prolonged vasoconstriction secondary to a physical, or functional, reduction in the vascular lumen. This luminal reduction may be caused by or associated with hypertrophy of the vascular muscle wall (the media), the accumulation of atherosclerotic plaque, platelet agglutination, disturbed laminar flow or local inflammatory swelling and leukocytic accumulation. Any and all of these findings often occur with simple aging or in association with other systemic disease: diabetes, hypertension, dyslipogenesis, hyperinsulinemia, arteriosclerosis, thyroid disease, etc. Although vascular insufficiency at specific tissue sites is widely variable and not predictable with certainty, the fact that most COAG patients are over 50 years old makes the frequency of these risk factors and the frequency of vascular insufficiency, high in this clinical group. Any proposed therapy should attempt to reduce the negative influences of the above risk factors and reduce local optic nerve head vascular insufficiency, in addition to lowering the IOP. For example: A therapeutic reduction of those endothelial abnormalities which contribute to specific or generalized risk factors which compromise local vascular integrity, will reduce the potential for glaucomatous optic nerve failure where microvascular dysregulation is significant. If this reduction of vascular risk factors is united with a reduction in aqueous production or outflow resistance, the combined effects of a well-oxygenated, more pressure-resistant nerve head and reduced IOP will further decrease the potential for optic atrophy and blindness.

Glaucoma—Biochemistry of Present Treatment

Current non-surgical treatments of COAG are based upon a limited number of biochemical approaches and focus exclusively upon reducing IOP:

a. Enzyme poisons—representatives of this group are most frequently carbonic anhydrase inhibitors. Carbonic anhydrase is an enzyme found in the ciliary processes and is required by them in their production of aqueous humor from blood. The members of this group are usually administered in tablet dosage forms. Besides the development of renal stones, potassium loss is a constant concern, especially in patients using digitalis derivatives. New, topical forms of this group have appeared as eyedrops. However, carbonic anhydrase activity is also present in the cytoplasm of corneal endothelial cells. The long-term corneal effects of this form of these medications are unknown. To avoid systemic reactions, patients with sulfonamide allergies should not use these drugs.

b. Parasympathomimetics—pilocarpine-containing compounds are particularly widely prescribed and act by causing pupillary constriction. As the pupil constricts, the relational anatomy of the peripheral iris and the filtering trabeculum causes the openings in the trabeculum to enlarge; thus, mechanical resistance to the outflow of aqueous is reduced as the summed area of the openings is increased. These agents are delivered in eyedrop dosage forms. Frequent side effects include headache from iris spasm, decreased night vision from miosis and blurred vision in myopes especially.

c. Beta-blocking agents—this very widely used group of drugs block the beta-adrenergic sympathetic rete responsible for increased vascular flow to the ciliary processes and, thus, indirectly reduce the production of aqueous humor. They also increase aqueous outflow through the trabeculum by methods that are less clearly defined. These agents are delivered in eyedrop dosage forms but must be used with great caution in patients with low blood pressure (orthostatic hypotension), sinus bradycardia or second/third degree heart block (severe bradycardia), obstructive pulmonary disease or bronchial asthma (acute bronchospasm) and diabetes (masking of hypoglycemia). They result in impotency in a significant number of men. There is contested evidence that ocular beta-blocking agents generally reduce blood flow to the posterior segment of the eye; some products are stated to have less significant bronchospastic side effects than others.

d. Topical prostaglandin analogs—this very new group of anti-inflammatory eyedrops presumably reduces IOP by increasing the outflow of aqueous through the trabeculum by widening the intra-trabecular space and, perhaps, by reducing platelet aggregation. Their use is associated with progressive and possibly permanent change in iris color to brown and some embryocidal outcomes in laboratory animals. Women of reproductive age and nursing women should avoid their use.

All of these treatment modes have significant and unavoidable, potential or demonstrable, local or systemic side effects or toxicities that directly contraindicate their use, reduce patient compliance or are worrisomely interactive with other systemic pharmaceuticals. These side effects may be serious even with conjunctival delivery by eyedrop dosage forms. Nevertheless, these medicaments represent today's entire medical armamentarium for the treatment of glaucoma.

SUMMARY OF THE INVENTION

The present invention resides in pharmaceutical preparations for use as oral dosage forms, transmembrane delivery or electrophoretic delivery forms. The preparations contain specific therapeutic biofactors and biomolecules selected because of their particular and critical physiological effects. These are combined in highly defined groups and amounts to achieve maximum complementarity of action.

This invention prevents optic nerve damage and visual loss, not by a focus restricted to the reduction of IOP, although it does have pressure-lowering capability, but by improving local and systemic endothelial health. This results from the advantageous modulation of intracellular calcium waves, the maintenance of vascular intraluminal fluidity by increasing cellular levels of nitric oxide, by augmenting the beneficial effects achieved by producing increased levels of vascular guanosine 3', 5'-cyclic monophosphate (cGMP) and by reducing the vascular risks associated with hyperinsulinemia secondary to reduced insulin sensitivity.

Increased cGMP results in: increased local blood flow, an increase in reparative endothelial cell proliferation, reduced endothelial permeability, the inhibition of vascular smooth muscle proliferation and the inhibition of cellular (including neuronal and glial) apoptosis (vide infra, cGMP Core Group).

In addition to providing the molecular radical necessary for the production of cGMP via the enzyme guanylate cyclase, NO is antithrombotic and reduces the activity of the potent vasoconstrictor ET-1 (vide infra, Cell Membrane Integrity Group).

Smoking, obesity, high fat diets and increasing age with its associated elevations of TNF-α and increased incidence of NIDDM are associated with hyperinsulinemia and reduced insulin sensitivity. Hyperinsulinemia and reduced insulin sensitivity, which may exist in 25% of the general population, is associated with disturbed vascular laminar flow, endothelial dysfunction, dyslipogenesis and hypertension—in brief, hyperinsulinemia is associated with vascular insufficiency and vasoconstriction. The COAG population is mainly an older age group. The COAG population is not immune from the existence of smoking, obesity, NIDDM, background levels of hypertension, etc. To the extent hyperinsulinemia and reduced insulin sensitivity exist in a significant portion of the general population, they also exist in the glaucoma population and are risk factors for glaucoma patients. The reduction of hyperinsulinemia by improving insulin sensitivity will reduce vascular factors that put the glaucomatous optic nerve at risk (vide infra, Hyperinsulinemia Modulation Group).

In glaucoma patients with elevated, normal or low IOP who are at risk of chronic glaucomatous visual loss, these combined vascular improvements maximize the potential for the success of current therapeutic regimens and minimize the risk of failure with progressive morbidity. The invention avoids the manifold side effects and therapeutic risks associated with all current glaucoma medications and positively influences both glaucoma risk factors: elevated intraocular pressure and compromised optic nerve vascularity.

The components within the invention are organized into four functionally interrelated and interdependent groups: 1. Cyclic GMP Core Group, 2. Calcium Wave Modulation Group, 3. Cell Membrane Integrity Group and 4. Hyperinsulinemia Modulation Group. The recitation of any component as a metal without specifying a charge or oxidation state in this specification or in the claims includes the metal in ionized form such as in a salt or bound form such as in an oxide or other chemical compound.

A. Cyclic GMP Core Group

The beneficial effects of the components of the cGMP Core Group of the invention are achieved by increasing cGMP. This results in increased blood flow, increased endothelial cell proliferation, reduced endothelial permeability, inhibited vascular smooth muscle proliferation and a lowered rate of both neural and glial apoptosis. The beneficial effects of the cGMP Core of the invention are amplified by Calcium Wave Modulation and improved Cell Membrane Integrity and extended even further by Hyperinsulinemia Modulation.

Components

L-arginine This is the precursor of NO via Type III NOS and ultimately cGMP. L-arginine is the backbone of the cGMP Core Group of the invention. An increase in the pool of available L-arginine has been shown to increase levels of vascular NO. There is evidence that NO directly modulates intracellular $Ca^{+2}$ oscillations by blocking smooth endoplasmic reticular $Ca^{+2}$ release and enhancing $Ca^{+2}$ extrusion (vide infra, Calcium Wave Modulation Group). If NO is inadequate a tonic, ET-1 vasoconstrictive response occurs. This again illustrates the integration and interdependence of the three biofactor Groups and the basis for their inclusion in this invention.

N-acetylcysteine (NAC) NAC is a glutathione (GSH) precursor used in the invention. Although GSH itself is very poorly absorbed (if at all) from oral dosage forms, the intestinal absorption characteristics of NAC are satisfactory. GSH supplies a thiol reservoir used as a carrier for NO, thereby acting as cellular "delivery system" for the otherwise evanescent NO. GSH causes a concentration-dependent increase in blood flow that is mediated by a NO and guanylate cyclase-dependent mechanism. This is probably due to the reaction between GSH and peroxynitrite forming S-nitrosoglutathione, a strong NO donor. GSH acts in concert with ascorbate to inhibit the tyrosine nitration of peroxynitrite. The latter nitration process leads to the severe membrane damaging effects of peroxynitrite. Additionally, GSH supplies the substrate for glutathione peroxidase, which quenches hydrogen peroxide and reduces its conversion to OH— (a highly toxic radical). It also lessens RBC microviscosity, thus augmenting blood flow in the microvasculature. GSH additionally stimulates superoxide dismutase (SOD) an activity which reduces the toxic effects of the superoxide radical.

Ginkgo biloba extract (EGB) EGB significantly increases end diastolic velocity in the ophthalmic artery thereby providing neuroprotection against glaucomatous optic neuropathy. EGB exerts its cerebral vasorelaxation via nitric oxide pathways; by inhibiting induction of iNOS mRNA and by scavenging iNOS-induced NO in macrophages. These complementary actions physiologically adjust the levels of both eNO and iNO.

Riboflavin Riboflavin is critical for electron transfer (the NADPH cycle) and is required to activate Type III NOS which enables the production of NO from L-arginine.

Folic Acid Folic acid stimulates endogenous tetrahydrobiopterin ($BH_4$) regeneration, which is an essential cofactor required for conversion of L-arginine to NO under the influence of eNOS Type III within the endothelial cell membrane. Folic acid also reduces the catabolism of NO and counters the reduced bioavailability of endothelial derived NO. Plasma levels of homocysteine are effectively lowered by folic acid, thus directly reducing the potent vasoconstrictive, endothelial cytotoxicity and thrombotic effects of homocysteine. Increased plasma levels of homocysteine represent an independent risk factor for atherothrombosis and reduced blood flow. Reducing homocysteine-induced endothelial dysfunction complements the Cell Membrane Integrity Group of this invention. The three key, unique biofactors in favorably altering homocysteine metabolism are included in the invention: folic acid, pyridoxine and cyanocobalamin ($B_{12}$).

$B_{12}$ $B_{12}$ in the formulation avoids the silent anemia that otherwise may result from the use of folic acid by itself. This is of particular importance in the age group afflicted with clinically progressive glaucoma, since hypochlorhydria in the elderly results in poor absorption of $B_{12}$ Pyridoxine Pyridoxine complements folic acid in reducing plasma homocysteine. Inducible nitric oxide synthase (iNOS) within activated macrophages contributes to the inflammation that characterizes early atherogenesis and may, in part, account for the adverse vascular effects of hyperhomocysteinemia. Evidence suggests that the expression of iNOS (a Type II gene product) in vascular smooth muscle cells may, in part, promote atherosclerosis by increasing local oxidative stress caused by toxic local levels of NO. However, the incorporation of pyridoxine and folic acid lessens the conversion of L-arginine to toxic levels of homocysteine-induced NO from iNOS Type II within activated macrophages, adding an element of safety to the invention B. Calcium Wave Modulation Group Calcium ($Ca^{+2}$) is a critically important intracellular messenger. Its intracellular signaling, which occurs in frequency modulated waves, can be modified by therapeutic calcium channel blockers which change the amplitude of $Ca^{+2}$ entering the cell. In disease or age, damage to a cell membrane increases membrane permeability and increases the amplitude of $Ca^{+2}$ entering the cell. This modulated signaling requires a fine balance between $Ca^{+2}$ flow patterns of the cell membrane, the plasma and the endoplasmic reticular substances and $Ca^{+2}$ flow patterns within and from the cytoplasm. Enzymes control many of these orchestrated $Ca^{+2}$ waves and magnesium ($Mg^{+2}$) is a key cofactor. Similarly, the amino acid taurine improves cellular $Ca^{+2}$ dynamics and is functionally complementary to $Mg^{+2}$.

Components $Mg^{+2}$ By a variety of mechanisms, $Mg^{+2}$ functions both intracellularly and extracellularly to optimize the cytoplasmic free $Ca^{+2}$ level. Excess cytoplasmic free $Ca^{+2}$ has the deleterious effect of leading to an increase in ET-1, with its associated decrease in blood flow, platelet aggregation and cell apoptosis. For these reasons correction of $Mg^{+2}$ deficiency exerts antihypertensive, antithrombotic and anti-atherosclerotic effects. It is important that $Mg^{+2}$ accomplishes this without interfering with normal $Ca^{+2}$ intracellular signaling. (Unfortunately pharmaceutical calcium channel blockers used clinically at effective doses have gross, amplitude driven, essentially uncontrolled effects on $Ca^{+2}$ cellular signaling.) $Mg^{+2}$ deficiencies are widespread in the elderly glaucomatous population: this is especially true in patients with normal renal function who also have diabetes—another disease common in upper age groups.

Taurine Taurine is a conditionally-essential amino acid which is not utilized in protein synthesis, but rather is found free or in simple peptides. It has been shown that a deficient dietary level of taurine is associated with a variety of pathologies, including retinal degeneration. Taurine is important for the modulation of cellular $Ca^{+2}$ levels, cell membrane stabilization and osmoregulation. Clinically, taurine has been used with varying degrees of success in the treatment of several conditions, including macular degeneration and Alzheimer's disease. There is evidence that taurine has an effect on reducing toxic effects on neurons. While taurine increases cytosolic $Ca^{+2}$ transients in cardiac cells (and thus has positive inotropic activity), in other cells it tends to reduce cytosolic $Ca^{+2}$ consistent with its role as a modulator of $Ca^{+2}$ intracellular signaling. Similar to $Mg^{+2}$, taurine lowers elevated blood pressure, retards cholesterol-induced atherogenesis, prevents arrhythmias, and stabilizes platelets and cell membranes. Its favorable modulation of $Ca^{+2}$ signaling complements the similar action of $Mg^{+2}$ and its stabilization of cell membranes augments the components of the Cell Membrane Integrity Group of this invention.

C. Cell Membrane Integrity Group

The plasma and endoplasmic reticular membranes consist of a bilayer of amphipathic phospholipids. These cell membranes provide a fluid barrier with selective permeability and selective active-transfer mechanisms. The membranes house protein molecules in arrangements that support their functionality and provide a surface consistent with the needs of ligands. In the case of the vascular endothelium, this arrangement must provide a physiologic surface that is proper both for circulating cells and favorable luminal flow. This is a tall order. If the cell membrane loses its integrity, Calcium Wave Modulation is impossible and NO is induced into iNOS Type II inflammatory status. These events lead to further loss of membrane integrity, becoming the proverbial circle in a spiral of vascular degradation, local hypoxia, and atrophy/apoptosis.

Components

D,α-Tocopherol Tocopherol is the main defense against the peroxidation cascade within the lipid layer of cell membranes. The latter is the principal cause of the loss of cell membrane integrity in many pathologic and, probably, aging states of vascular and neuronal cells. D,α-tocopherol preserves superoxide dismutase (SOD), a front line enzyme involved in free radical defense; this is especially true for toxic hydrogen peroxide defense. As detailed below, the other components of the invention which complement this D,α-tocopherol hydrogen peroxide defense are selenium (Se), ubiquinone, quercetin and, indirectly, ascorbate.

Ascorbate Phase transfer rejuvenation of tocopherol must occur to maintain and amplify D,α-tocopherol's chain-breaking effect on lipid peroxidation, the ultimate protection from free radical damage to cell membranes. Synergism with tocopherol is shared by two components of this group: ubiquinone and quercetin. In addition, ascorbate improves impaired acetylcholine-induced vasodilation by mechanisms linked to NO formation. Although the free radical scavenging abilities of ascorbate are well established, its complementary actions for free radical defense with other components of this invention may be less well known: with taurine for $HOCl^-$ defense; with GSH or Se for hydrogen peroxide defense; with SOD, zinc or copper for superoxide defense. Superoxide and excess NO form peroxynitrite, an important tissue-damaging species; GSH and ascorbate protect efficiently in this area, perhaps because ascorbate mimics GSH's stimulation of SOD activity.

Ubiquinone (CoQ10) In addition to phase transfer rejuvenation of D,α-tocopherol, CoQ10 complements tocopherol by directly inhibiting lipid peroxidation.

As one example: LDL3, the densest of the three LDL subfractions, shows statistically significant lower levels of CoQ10, a condition which is associated with higher hydroperoxide levels when compared with the lighter counterparts. After CoQ10 supplementation, although all three LDL subfractions increase their CoQ10 levels, LDL3 responds with the greatest and is associated with a significant decrease in hydroperoxide level. These results support the hypothesis that the CoQ10 endowment in subfractions of LDL lessens their oxidizability.

Quercetin Like D,α-tocopherol, quercetin quenches free radical chain reactions in cell membranes. Furthermore, the interaction of quercetin with the lipids of the cell membrane occurs in the polar zone of the lipid bilayers, thereby providing a defense against free radicals attacking the membrane surface. Quercetin also has the potential to reduce oxidized alpha-tocopherol. This function of quercetin is enhanced by ascorbate even under conditions in which ascorbate functions as a prooxidant when used alone—as when too much ascorbate is ingested. This antioxidative enhancement is attributed to the involvement of ascorbate in the phase transfer rejuvenation of quercetin after it has been oxidized during interaction with free radicals. The relationship between quercetin, ascorbate and D,α-tocopherol is clearly synergistic.

Copper ($Cu^{+2}$) $Cu^{+2}$ is a cofactor for SOD and is essential for cardiovascular homeostasis. Dietary $Cu^{+2}$ is necessary for microvascular control mechanisms affecting the regulation of peripheral blood flow. NO-mediated arteriole vasodilation is compromised when $Cu^{+2}$ is deficient. This functional deficit of NO can be reversed by the addition of Copper-Zinc SOD, suggesting that degradation of NO by superoxide anion occurs unopposed during $Cu^{+2}$ and $Zn^{2+}$ deprivation.

Zinc ($Zn^{2+}$) $Zn^{2+}$ is a cofactor for, and is reported to be an inducer of, SOD. However, large amounts of $Zn^{2+}$ should be avoided since this overload may paradoxically convert $Zn^{2+}$ into a prooxidant by reducing the antioxidant effect of SOD. $Zn^{+2}$ supplements reduce the ferroxidase activity of serum and the oxidant activity of erythrocyte superoxide. A detrimental effect on $Cu^{+2}$ levels occurs after supplementation with a moderate amount of $Zn^{+2}$. $Zn^{+2}$ is necessary for nucleic acid and protein synthesis, the formation of sulfated molecules, the formation of retinal reductase and of SOD, and is required for the structure and activity of many ocular metalloenzymes. The highest concentration of $Zn^{+2}$ is measured in the eye, particularly in the pigment-containing components. Although the exact mechanism of its molecular and cellular functions is largely unknown, the essentiality of this element in various compartments of the eye (including the retina, choroid, cornea and lens) is well established; $Zn^{+2}$ deficiency causes functional impairments in various parts of the eye. $Zn^{+2}$ related toxicities also have been shown in human and animal eyes.

Selenium (Se) Se is the enabling cofactor for glutathione peroxidase thereby enabling the scavenging of hydrogen peroxide and avoiding its progression to the dangerous hydroxyl radical. It has also been shown to influence favorably the coagulopathy associated with endothelial dysfunction and improve RBC microviscosity. Biological interaction between Se and a number of other elements, including $Cu^{+2}$, is required for the activity and stable structure of many ocular metalloenzymes and render Se less toxic than when it is present alone.

D. Hyperinsulinemia Modulation Group

Silent, undiagnosed hyperinsulinemia is very common in the general population. It is associated with disturbed vascular laminar flow, endothelial dysfunction, dyslipogenesis and hypertension—in brief, hyperinsulinemia is associated with widespread vascular insufficiency and vasoconstriction. As discussed above, these vascular abnormalities place the optic nerve of the glaucoma patient at risk of failure. Since the chronic glaucoma population exists mainly in an upper age bracket, a foundation of age-related vascular insufficiencies already exists. If these fundamental vascular risks are coupled with the additional presence of hyperinsulinemia and its attendant vascular abnormalities, the potential for optic nerve head failure is greatly increased. Treatment or supplement approaches to glaucoma must provide for attenuation of presumed or diagnosed hyperinsulinemia and improvement of insulin sensitivity if undesirable dysvascular perturbations are to be avoided.

Components

Chromium (Cr) Cr, a cofactor for insulin, is an essential nutrient required for carbohydrate and fat metabolism. Cr decreases hyperinsulinemia by improving insulin binding, increasing the number of insulin receptors, improving insulin internalization, elevating beta cell sensitivity and insulin receptor enzymes; in general, it results overall in improved insulin sensitivity. The estimated safe and adequate daily dietary intake for Cr is 50 to 200 micrograms. Dietary intake of Cr for humans is suboptimal. Most current, Western diets contain less than 30 micrograms of Cr per day and this is exacerbated by increased intake of refined foods that contain little Cr and increase Cr losses. Furthermore, the Cr requirement is believed to increase with increased insulin intolerance. Trivalent Cr has a very large safety range, with no evidence of Cr toxicity at levels up to 1 mg per day.

Vanadium (V) V reduces hyperinsulinemia. As an insulin cofactor, V modulates insulin metabolic effects by enhancing insulin sensitivity and prolongs insulin action and it has an ability to 'bypass' defects in insulin signaling.

α-Lipoic Acid α-lipoic acid, is a cofactor in dehydrogenase complexes that improve insulin-responsive glucose utilization producing a positive effect on insulin-stimulated glucose uptake. It is complementary to the Cell Membrane Integrity Group of this invention in that it is a potent antioxidant in both fat- and water-soluble mediums. Furthermore, these antioxidant activities exist for its oxidized and reduced forms. α-lipoic acid is capable of regenerating ascorbic acid from dehydroascorbic acid, directly regenerating vitamin C and indirectly regenerating vitamin E. It increases intracellular GSH, that most important thiol antioxidant, and it limits protein glycation and, consequently, the associated Advanced Glycation Endproducts (AGE). α-lipoic acid reduces AGE albumin-induced NF-kappaB mediated transcription and expression of endothelial genes, and thereby AGE albumin-induced endothelial dysfunction.

Nicotinamide Nicotinamide improves glucose utilization (either directly or indirectly) by improving $Zn^{+2}$ uptake. By so doing it lessens hyperinsulinemia. $Zn^{+2}$ complements the biofactors of the Cellular Membrane Integrity Group of this invention by improving blood rheology by reducing plasma oxLDL levels. As an NAD+ precursor, nicotinamide protects against oxidative stress and DNA damage by up-regulating the stress response genes GAPDH and G6PD.

Melatonin Melatonin is an indole produced in the pineal and the retina which, among other effects, increases insulin sensitivity and reduces hyperglycemia. Melatonin production declines markedly after age 45 in parallel with an increasing occurrence of hyperinsulinemia and glaucoma. Although the exact role of melatonin in human glucose regulation is not completely defined, circadian rhythmicity and sleep modulate glucose tolerance: two central nervous system processes, which are influenced by melatonin. In the presence of a constant stimulus (e.g. intravenous glucose infusion), blood glucose levels increase from morning to evening and further increase until the middle of sleep, when a decline towards morning levels is initiated. This 24-hr variation is related to the balance between insulin sensitivity and insulin secretion. Melatonin is likely to play its role in the mechanisms underlying glucose regulation via its actions on the suprachiasmatic nucleus. Supplemental melatonin for glaucoma patients to reduce hyperinsulinemia is therefore physiologically sound, and would be appropriate. This is even more important for the many glaucoma patients treated with beta-blockers which reduce melatonin production. Furthermore, the melatonin requirement is believed to increase with increased insulin intolerance during the day as well as night. In youth the melatonin levels decline during the day to about 15% of peak night values but do not reach zero.

DETAILED DESCRIPTION OF THE INVENTION AND PREFERRED EMBODIMENTS

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, and liquid solutions, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological process in some manner. "Activity" is the ability to perform the function, or to induce or affect the process. Active agents and ingredients are distinguishable from excipients such as carriers, vehicles, diluents, lubricants, binders, and other formulating aids, and encapsulating or otherwise protective components.

"Delivery vehicle" is a composition, which comprises one or more active agents, and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

"Vasoconstriction" is the reduction of the cross section of a blood vessel lumen, inhibiting the free flow of blood through the vessel. Vasoconstriction can arise from vasospasm, deposits on or in the lumen wall or from the thickening of the wall material due to excessive growth or proliferation of one or more of the wall layers.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Solubility and Gastrointestinal Absorption Characteristics of the Components

Ions, heavy metals and biomolecules are absorbed through the gastrointestinal epithelium by a variety of mechanisms; some passively according to concentration gradients, others require active transport by membrane-bound protein molecules that may be distributed differently along the course of the gastrointestinal tract and which may be more or less selective. Some gastrointestinal absorption of ions, heavy metals or biomolecules may occur by more than one mechanism.

The mucus layer covering the surface of the gastrointestinal tract may act as a barrier to drug absorption; therefore, the self-diffusion coefficients of drugs with different physicochemical properties in gastrointestinal mucus are important considerations. The most important physicochemical characteristic influencing the diffusion coefficient of smaller molecules through gastrointestinal mucous appears to be their lipophilicity; molecular size appears to have more influence for larger peptide drugs. Electrical charge has only a minor effect on the diffusion coefficients across the intestinal barrier.

Some ions, heavy metals or biomolecules may enhance or inhibit the gastrointestinal absorption of others. Substantial data is not available at the present time regarding this competitive absorption. However, where it is available, the quantities listed in the final formulations of the invention take these absorption characteristics into account.

Absorption data are included when available, otherwise qualitative comments based on molecular structure are included.

|   |   | cyclic GMP (core) Group |
|---|---|---|
| a) | L-Arginine | |
|   | Absorption: | Absorption of L-arginine is highest in the upper three gastrointestinal regions and least in the ileum. But no preferential site of absorption has been found. |
|   | Pharmacokinetics: | The gastrointestinal uptake of dietary arginine when the stomach is in the "fed" state is about 20% to 38%. |
| b) | N-acetylcysteine (NAC) | |
|   | Absorption: | NAC is used as a precursor of GSH. Intestinal absorption of NAC is satisfactory. After an oral dose of 200 to 400 mg of NAC peak plasma concentration is achieved within 1 to 2 hours. The hours. The upper jejunum is a principal site of GSH absorption, which, however, is very limited. This low GSH bioavailability is not increased by high doses. Orally administered GSH at reasonable levels does not affect the circulating concentrations of GSH, whereas NAC administration increases the GSH content in lungs, blood and/or liver. Oral NAC inhibits gastric emptying. |
|   | Pharmacokinetics: | The administration of NAC increases hepatic cysteine placing it on a path for the modulation of systemic GSH levels. Pharmacokinetics and pharmacodynamic studies of NAC demonstrate elevated GSH levels in plasma, RBC and peripheral blood lymphocytes (PBL), elevated cysteine levels in plasma and increases in two GSH-metabolizing enzymes, glutathione S-transferase and oxidized glutathione reductase, in PBL. These studies have established NAC as the precursor of GSH. |
| c) | Riboflavin | |
|   | Absorption: | Saturable (active transport) and nonsaturable, |

| | | -continued |
|---|---|---|
| | | energy-independent diffusion of riboflavin occurs throughout the rat small intestine. |
| | Pharmacokinetics: | A small circadian variation in riboflavin occurs, with plasma concentrations and urinary excretion of riboflavin being low during the afternoon. Since riboflavin may increase gastrointestinal iron absorption it is included in the delayed release portion of the combination dosage form of the invention. |
| d) | Folic acid | |
| | Absorption: | Folic acid is absorbed in the first 30 cm of the jejunum by both saturable and diffusional routes. |
| | Pharmacokinetics: | Folic acid is a coenzyme which humans, unlike bacteria, cannot synthesize de novo, therefore it is a dietary essential. Folic acid is converted to the active coenzyme tetrahydrofolate (THF) by repeated hydrogenation of the pterin ring. The coenzyme THF is then capable of one-carbon-residues transfers of different oxidation states. |
| e) | Cyanocobalamin ($B^{12}$) | |
| | Absorption: | The ileum is the major site of absorption of vitamin $B^{12}$, where its intestinal absorption is facilitated by two receptors and two transporters. |
| | Pharmacokinetics: | In nature, vitamin $B^{12}$ is only exceptionally met in its free form. It is almost always associated with a binder. Alimentary vitamin $B^{12}$ released from its protein complexes by culinary preparation and gastric secretions, is combined with haptocorrin. In the duodenum, haptocorrin is partially degraded by pancreatic enzymes and intraluminal pH and $B^{12}$ is attached to intrinsic factor for transfer. This combination of the vitamin can then be "caught" by the ileal receptor. |
| | Pyridoxine | |
| | Absorption: | Pyridoxine absorption in the jejunum (rat) is non-saturable and consistent with passive diffusion. The gastrointestinal concentrations of pyridoxine in various intestinal segments tend to parallel those of riboflavin, suggesting some similarity of absorption characteristics. While the gastro-intestinal absorption characteristics may be similar to riboflavin, it is unclear if it shares the iron absorption enhancement properties of the latter. |
| | Pharmacokinetics: | Studies have suggested that a physiological dose of pyridoxine is transformed to pyridoxal in the intestinal tissues and then released in this putative active form into the portal blood. |
| | | Calcium Wave Modulation Group |
| f) | Magnesium Taurate | |
| | Absorption: | Taurine uptake across the intestinal brush border membrane of the adult cat seems not to require a specific transport mechanism, although the steady-state uptake of taurine by rat intestinal cells is saturable. |
| | Pharmacokinetics: | Taurine, even at a low concentration, seems to enhance drug absorption due to its effect on the permeability characteristics of the mucosal membrane Bile salts are synthesized in the liver from cholesterol conjugated with taurine. Within the gastrointestinal lumen these bile salts play an essential role in lipid absorption and fat transport. |
| g) | Magnesium Oxide (MgO) | |
| | Absorption: | $Mg^{2+}$ is absorbed by active transport in the ileum although there is limited passive diffusion throughout the intestine. |
| | Pharmacokinetics: | MgO must be converted to magnesium chloride in the acid milieu of the stomach. However, there is |

| | | -continued |
|---|---|---|
| | | a maximum $Mg^{2+}$ absorption of 8 mEq per meal with a curvilinear falloff and $Mg^{2+}$ absorption is negatively influenced by dietary protein: soybean protein, when compared with casein, decreases $Mg^{2+}$ absorption through its phytate component. These both speak to the importance of multiple doses per day. |
| | | Cell Membrane Integrity Group |
| h) | D,α-Tocopherol | |
| | Absorption: | The gastrointestinal absorption of dietary D,α-tocopherol is dependent upon the simultaneous digestion and absorption of the fat in which the vitamin is solubilized. Taurine may enhance D,α-tocopherol absorption (vide supra, p 22.). The site of D,α-tocopherol absorption is probably the proximal small intestine. |
| | Pharmacokinetics: | Evidence suggests that further uptake of the tocopherols occurs in the deep crystal zone of the colonic mucosa where actively proliferating cells extract nutrients from the systemic circulation. |
| i) | Magnesium Ascorbate | |
| | Absorption: | Natural and synthetic ascorbates (and folates) are avidly absorbed in the first 30 cm of jejunum. |
| | Pharmacokinetics: | There is no pharmacokinetic justification for the use of megadoses of ascorbate (vit C). As the daily oral dose vit C is increased, the concentration of ascorbic acid in the plasma and other body fluids does not increase proportionally, but approaches an upper limit. Analysis indicates that both saturable gastrointestinal absorption and nonlinear renal clearance act additively to produce a ceiling effect in plasma concentrations. As a consequence of this ceiling effect, there is no pharmacokinetic justification for the use of extremely large doses of vit C. Vit C must be considered a physiological factor essential for the absorption of dietary iron; recurrent renal stone formers and patients with renal failure who have a defect in vit C or oxalate metabolism should restrict daily vit C intakes to approximately 100 mg. |
| j) | Ubiquinone (CoQ10) | |
| | Absorption: | Supplemental oil-based capsules elevate CoQ10 in plasma by 178% while granular preparations increase CoQ10 in plasma by 168%. Each is therefore an acceptable delivery vehicle. |
| | Pharmacokinetics: | After oral administration of 100 mg of d5-CoQ10 to 16 healthy male subjects, the mean plasma CoQ10 level attained a peak of 1.004 +/− 0.370 micrograms/ml at 6.5 +/− 1.5 h after administration, and the terminal elimination half-life was 33.19 +/− 5.32 h. In most of the subjects, plasma d5-CoQ10 showed a second peak at 24 h after dosing. This unusual plasma level curve can be well described by a compartment model based upon the assumption that absorbed CoQ10 is taken up by the liver and then transferred mainly to very low density lipids (VLDL) and redistributed from the liver to the systemic blood. |
| k) | Quercetin | |
| | Absorption: | Intestinal absorption of quercetin is 24% +/− 9%. Absorption is enhanced by conjugation with glucose. |
| | Pharmacokinetics: | Quercetin can be absorbed by humans from dietary sources in high enough concentration to increase the overall antioxidant activity of the plasma. Quercetin, however, has a strong affinity for protein. |
| l) | Copper ($Cu^{+2}$) | |
| | Absorption: | 30–40% of $Cu^{+2}$ GI absorption is via a carrier-mediated transport but because aging probably |

| | | -continued |
|---|---|---|
| | | decreases the efficiency of $Cu^{+2}$ homeostasis, higher plasma $Cu^{+2}$ concentrations are sometimes found in the elderly. A minimum dietary $Cu^{+2}$ requirement of between 0.4 and 0.8 mg/d is needed to replace daily copper losses of approximately 1.3 mg/day. Supplementation with even a moderate amount of $Zn^{+2}$ has a detrimental effect on $Cu^2$ levels. |
| | Pharmacokinetics: | The human gastrointestinal system can absorb 30–40% of ingested $Cu^{+2}$. Dietary supplements of minerals with similar chemical characteristics (e.g., $Zn^{+2}$) can reduce $Cu^{+2}$ absorption and manipulation of the fiber content of the diet may have an indirect effect on $Cu^{+2}$ bioavailability by altering the bioavailability of these mineral antagonists. Proteins, organic acids other than ascorbic acid (or agents that form low-molecular-weight chelates) and soluble carbohydrates tend to improve $Cu^{+2}$ absorption. |
| m) | Zinc ($Zn^{+2}$) | |
| | Absorption: | Absorption of $Zn^{+2}$ ranges from 40 to 86%. About 37% of ingested $Zn^2$ enters the plasma and gastrointestinal absorption is essentially completed by 4 hours. The duodenum and ileum are important sites for rapid $Zn^{+2}$ absorption. A continuous, slower absorption of $Zn^{+3}$ may take place in the jejunum while the stomach, cecum and colon appear to be insignificant sites of absorption. |
| | Pharmacokinetics: | Mean plasma $Zn^{+2}$ increases only 37% above pre-load levels in face of an 11-fold increase in intake. |
| n) | Selenium (Se) | |
| | Absorption: | Sodium selenite is absorbed slowly, possibly by simple diffusion through the intestinal mucosa. |
| | Pharmacokinetics: | Thiols positively influence mucosal uptake of Se. As an example, L-cysteine stimulates Se uptake in the middle and distal jejunum and cecum but not in the proximal jejunum. This effect is maximal in the distal jejunum. Also, the absorption of amino acid-bound Se is accelerated by specific amino acid active transport mechanisms in the gut mucosa. |
| o) | Melatonin | |
| | Absorption: | Ingestion of 3 mg melatonin causes a marked increase in serum melatonin (3561 +/− 1201 pG/mL) within 20 min. Although this is followed by a gradual decrease, the level still remains higher than the basal level at 240 min after ingestion. |
| | Pharmacokinetics: | When huge doses of melatonin (80 mg) are administered orally, changes in serum melatonin levels are best described by a biexponential equation with an absorption constant (ka) of 1.72 h-1 (half-life = 0.40 h) and an elimination constant (kel) of 0.87 h-1 (half-life = 0.80 h). Peak serum melatonin occurs 60–150 min after its administration, remaining stable for approximately 1.5 hours. |
| p) | Ginkgo Biloba Extract (EGB) | |
| | Absorption: | The absorption of EGB is about 60%. Different formulations of Ginkgo biloba extracts (e.g., capsules, drops or tablets) appear to be bio-equivalent. |
| | Pharmacokinetics: | The ginkgolides and bilobalides, which are compounds extracted from the dried leaves of the Ginkgo biloba tree, have high bioavailability when given orally during fasting. The bioavailability coefficients (FAUC) have mean (+/−SD) values equal to 0.80 (+/−0.09), 0.88 (+/−0.21) and 0.79 (+/−0.30) for Ginkgolide A, Ginkgolide B and Bilobalide respectively. Food intake does not change FAUC quantitatively but increases Tmax. |

| | | -continued |
|---|---|---|
| | | Hyperinsulinemia Modulation Group |
| a) | Chromium (Cr) | |
| | Absorption: | It has been proposed that 90% of American's diets are deficient in the essential trace element, Cr. Even with significant dietary Cr intakes, only a small fraction of the ingested Cr, is absorbed; most is excreted in the stool. Urinary Cr is constant from day to day. The Cr balances (apparent net retention) remain positive, however, indicating equilibrium. In one small study, the average apparent net absorption of Cr was 1.8%. |
| | Pharmacokinetics: | Principal Cr concentrations are found in the liver, spleen, soft tissue, and bone. Most nutrients and metabolites do not alter Cr retention and distribution. The regulation of Cr homeostasis appears to be at the level of excretion. |
| p) | Vanadium (V) | |
| | Absorption: | V has been found to be orally active in lowering plasma glucose levels, although most ingested V is eliminated unabsorbed by fecal excretion. Organic chelation of V may facilitate uptake into vanadium-sensitive tissues. |
| | Pharmacokinetics: | The insulin-mimetic action of V persists after withdrawal of V supplementation. This invention includes a pulsing of V administration to take advantage of this prolonged insulin-mimetic effect and to reduce the possibility of potential chronic-use toxicity. There is no development of tolerance with long term oral V administration. |
| q) | α-Lipoic Acid | |
| | Absorption: | Non-saturable kinetics of α-lipoic acid in healthy volunteers are demonstrable from single oral doses in the range of 200 to 600 mg. |
| | Pharmacokinetics: | In one study, the absolute bioavailability of lipoic acid in humans after a 200 mg oral dose was 29.1 +/− 10.3%. In rats given oral doses of ($C_{14}$) α-lipoic acid, the area of ($C_{14}$) α-lipoic acid in the plasma concentration-time curve (AUC) was 66% of that following similar intravenous administration. |
| r) | Nicotinamide | |
| | Absorption: | Immediate release dosage forms achieve higher plasma levels than sustained release. Formulations at high doses produce nonlinear kinetics, e.g., a 10-fold increase in the dose of standard nicotinamide produces a 62-fold increase in the AUC. |
| | Pharmacokinetics: | Nicotinamide is a derivative of the B vitamin niacin. There appears to be no significant difference in the kinetics of low dose standard nicotinamide (2.5 mg/kg) and low-dose, long acting nicotinamide (Enduramide) (6.7 mg/kg). Nonlinear kinetics are found with both formulations at higher doses. The AUC is significantly greater with the standard formulation, indicating a higher bioavailability. The AUC for standard nicotinamide is 1.7 times higher than that for Enduramide. |

Compositions, Formulations and Dosages

The amounts of the primary components of the pharmaceutical preparation of this invention can vary, although in preferred preparations the components are present in amounts lying within certain ranges. Expressed in terms of the components and their preferred ranges are as follows:

TABLE I

| Component | Dosages in milligrams | |
|---|---|---|
| | Preferred | Most Preferred |
| A L-Arginine | 100 to 4500 | 400 to 2500 |
| N-acetyl-Cysteine | 75 to 2500 | 250 to 1000 |
| Gingkolides (EGB) | 7 to 250 | 25 to 100 |
| Riboflavin | 5 to 400 | 50 to 100 |
| Folic acid | 0.100 to 5.0 | 0.200 to 0.400 |
| Cyanocobalamin (B12) | 0.001 to 0.008 | 0.003 to 0.005 |
| Pyridoxine | 1.0 to 100 | 2.0 to 15 |
| B Magnesium ($Mg^{2+}$) | 50 to 500 | 155 to 310 |
| Taurine | 75 to 2500 | 250 to 1000 |
| C D,α-tocopherol | 15 to 1000 | 300 to 600 |
| Ascorbate | 30 to 3000 | 300 to 600 |
| Ubiquinone | 5 to 200 | 30 to 60 |
| Quercetin | 10 to 250 | 75 to 150 |
| Copper ($Cu^{2+}$) | 0.5 to 3.0 | 1.0 to 2.0 |
| Zinc ($Zn^{2+}$) | 2 to 50 | 5 to 10 |
| Selenium | 0.05 to 0.20 | 0.10 to 0.2 |
| D Chromium | 0.008 to 0.63 | 0.025 to 0.25 |
| Vanadium | 7.5 to 375 | 25 to 150 |
| Alpha-Lipoic Acid | 90 to 1500 | 300 to 600 |
| Nicotinamide | 3 to 375 | 10 to 150 |
| Melatonin | 0.05 to 10 | 0.25 to 5.0 |

L-ARGININE may be included in this invention as a free base or combined with the metallic cations contemplated by this invention—$Mg^{+2}$, $Cu^{+2}$ or $Zn^{+2}$—as metal L-arginine complexes which have the following formula:

[Arg] M X wherein,
a. Arg is the amino acid L-arginine or bis-L,arginine;
b. M is a metal ion taken from, $Mg^{+2}$, $Cu^{+2}$ or $Zn^{+2}$;
c. X is an anion taken from the group including hydroxides, halides, sulfates, acetates, ascorbates or bis-ascorbic acid salts.

N-ACETYL-CYSTEINE (NAC), mercaptopropionylglycine (MPG) or L-2-oxothiazolidine-4-carboxylate (OTC) may be included in this invention as a free base or combined with the metallic cations contemplated by this invention—$Mg^{+2}$, $Cu^{+2}$ or $Zn^{+2}$—as metal complexes which have the following formula:

[A] M X wherein,
a. A is cysteine, acetylcysteine, NAC, MPG or OTC;
b. M is a metal ion taken from the metallic cations contemplated by this invention: $Mg^{+2}$, $Cu^{+2}$ or $Zn^{+2}$;
c. X is an anion taken from the group including hydroxides, halides, sulfates, phosphates, acetates, ascorbates or bis-ascorbic acid salts.

α-LIPOIC ACID (LA) or thioctic acid (TA) may be included in this invention as a free base or combined with the metallic cations contemplated by this invention; $Mg^{+2}$, $Cu^{+2}$, $Zn^{+2}$ or $Se^{+2}$ as metal alpha-lipoic acid or thioctic acid complexes which have the following formula:

[A] M X wherein,
a. A is LA or TA;
b. M is a metal ion taken from, $Mg^{+2}$, $Cu^{+2}$, $Zn^{+2}$ or $Se^{+2}$;

c. X is an anion taken from the group including hydroxides, halides, sulfates, phosphates, acetates, ascorbates or bis-ascorbic acid salts.

or $[A]_2MX$ wherein,
a. A is LA or TA,
b. M is a metal ion taken from $Mg^{+2}$, $Cu^{+2}$, $Zn^{+2}$ or $Se^{+2}$;
c. X is an anion taken from the group including hydroxides, halides, sulfates, phosphates, acetates or ascorbates or bis-ascorbic acid salts.

L-ARGININE, N-ACETYL-CYSTEINE, TAURINE and α-LIPOIC ACID and metals of this invention; $Mg^{+2}$, $Cu^{+2}$, $Zn^{+2}$ or $Se^{+2}$ may also be included as bi-amide complexes in formulae of this invention with the following structure:

[A] M X wherein,
a. A is 2,N-thioctylarginine (2NTA), 2,N-thioctylcysteine (2NTCy), 2,N-thioctyllysine (2NTL), 2,N-thioctyltaurine (2NTT);
b. M is a metal ion taken from $Mg^{+2}$, $Cu^{+2}$, $Zn^{+2}$ or $Se^{+2}$;
c. X is an anion taken from the group including hydroxides, halides, sulfates, phosphates, acetates or ascorbates or bis-ascorbic acid salts, or $[A]_2MX$ wherein,
a. A is 2,N-thioctylarginine (2NTA), 2,N-thioctylcysteine (2NTCy), 2,N-thioctyllysine (2NTL), 2,N-thioctyltaurine (2NTT);
b. M is a metal ion taken from $Mg^{+2}$, $Cu^{+2}$, $Zn^{+2}$ or $Se^{+2}$;
c. X is an anion taken from the group including hydroxides, halides, sulfates, phosphates, acetates or ascorbates or bis-ascorbic acid salts.

TAURINE may be used in this invention in its free forms or complexed or both. Absorption characteristics and pharmacokinetics are described in the "Solubility and Gastrointestinal Absorption Characteristics of the Components" (vide supra, p. 19).

MAGNESIUM is present either as $Mg^{+2}$ salts or $Mg^{+2}$ complexes that release magnesium ion when ingested, or both. Examples of salts of $Mg^{+2}$ that can be used in this invention are acetate, acetyl-cysteinate, arginate, ascorbate, cutrate, lipoate, malate, oxide, stearate, sulfate and taurate. As an example of kinetics after ingestion, magnesium ascorbate is soluble in gastric fluid and the respective components are absorbed in the gastrointestinal tract. The ascorbate radical serves as an adequate source of vitamin C by conversion to ascorbic acid upon exposure to hydrochloric acid in the gastric fluid, while the magnesium ion is converted to soluble magnesium chloride. The satisfactory water solubility of magnesium ascorbate provides for a diffusional gradient of $Mg^{+2}$ in the upper small intestine where some passive absorption of $Mg^{+2}$ occurs. Magnesium oxide is converted to magnesium chloride in the acid environment of the stomach and offers the advantage of high ionic magnesium content, since 60% by weight of the magnesium oxide molecule is $Mg^{+2}$. Magnesium stearate is useful as a lubricant when compressing the composition into tablets, in addition to its use as a minor $Mg^{+2}$ source. Preferred $Mg^{+2}$ sources include magnesium ascorbate, magnesium taurate, magnesium oxide or one of the complexes described previously.

COPPER is present either as $Cu^{+2}$ salts or $Cu^{+2}$ complexes that release copper ion when ingested, or both. Absorption and pharmacokinetics are described above (vide supra, p.24). Examples of salts of $Cu^{+2}$ that can be used in this invention are arginate, lipoate, sulfate, and taurate. Preferred $Cu^{+2}$ sources include copper sulfate or one the complexes described previously.

ZINC is present either as $Zn^{+2}$ salts or $Zn^{+2}$ complexes that release zinc ion when ingested, or both. Absorption and pharmacokinetics are described above (vide supra, p.24). Examples of salts of $Zn^{+2}$ that can be used in this invention are acetate, arginate, lipoate, sulfate, and taurate. Preferred $Zn^{+2}$ sources include zinc acetate, zinc taurate or one the complexes described previously.

SELENIUM is present either as $Se^{+2}$ salts or $Se^{+2}$ complexes that release selenium ion when ingested, or both. Absorption and pharmacokinetics are described above (vide supra, p.24 ). Examples of salts of $Se^{+2}$ that can be used in this invention are acetate, arginate, lipoate, sulfate, and taurate. Preferred $Se^{+2}$ sources are L-selenomethionine, selenium from yeast or from the one of the complexes described previously.

CHROMIUM is present as $Cr^{+3}$ salts release chromium ion when ingested. Absorption and pharmacokinetics are described above (vide supra, p.25). Preferred $Cr^{+3}$ sources include chromium tripicolinate or chromium binicotinate.

VANADIUM is present as vanadium ($V^{2+}$ to $V^{5+}$) salts and release vanadium ion when ingested. Absorption and pharmacokinetics are described above (vide supra, p.26). Preferred vanadium sources include vanadyl sulfate or organic vanadium compounds, such as bis(maltolato)oxovanadium(IV).

D,α-TOCOPHEROL and its analogs and esters are D,α-tocopherol, D,α-tocopherol acid succinate, D,α-tocopherol nicotinate and D,α-tocopherol acetate. A particularly preferred form of vitamin E is D,α-tocopherol acid succinate or microencapsulated D,α-tocopherol nicotinate, especially for preparations in tablet form. The gastrointestinal absorption of dietary D,α-tocopherol is bile salt dependent and therefore is somewhat also dependent upon the simultaneous digestion and absorption of fat. The presence of dietary taurine, involved in the conversion of cholic acid to dexycholic acid in the gut, enhances D,α-tocopherol absorption. In these respects D,α-tocopherol absorption may be similar to that of vitamin A and the site of major vitamin A absorption is the proximal small intestine.

ASCORBATE is present either as ascorbic acid, metalloascorbate salts or complexes of ascorbate, or all of these (vide supra, p.29). Examples of metallic salts of ascorbate that can be used in this invention are $Mg^{+2}$, $Cu^{+2}$ or $Zn^{+2}$. Absorption and pharmacokinetics are described above (vide supra).

GINGKOLIDES (EGB), MELATONIN, UBIQUINONE, QUERCETIN and the B VITAMINS are present within this invention in their free forms. Absorption and pharmacokinetics are described above in "Solubility and Gastrointestinal Absorption Characteristics of the Components" (vide supra).

A slower, more sustained release of the active agents can be achieved by placing the active agents in one or more delivery vehicles that inherently retard the release rate. Examples of such delivery vehicles include polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., U.S.A.; and the cellulose acetate phthalate latex AQUATERIC®, available from FMC Corporation, New York, N.Y., U.S.A., and similar products available from Eastman-Kodak Co., Rochester, N.Y., U.S.A.

Acid-resistant films of these types are particularly useful in confining the release of magnesium lactate and magnesium citrate to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

In certain embodiments of the invention, the dosage form is a substantially homogeneous single layer tablet that releases all of its components into the stomach upon ingestion (vide infra). In some embodiments a sustained dosage form is used and in others both dosage forms are combined into a bilayer tablet. Examples of the preferred ranges for components in each layer are shown in Table II.

TABLE II

| Component | Dosages in milligrams | | % in Bilayer | |
|---|---|---|---|---|
| | Preferred | Most Preferred | Immed | Sustain |
| A L-Arginine | 100 to 4500 | 400 to 2500 | 75% | 25% |
| N-acetyl-Cysteine | 75 to 2500 | 250 to 1000 | 75% | 25% |

TABLE II-continued

| | Dosages in milligrams | | % in Bilayer | |
| Component | Preferred | Most Preferred | Immed | Sustain |
|---|---|---|---|---|
| Gingkolides (EGB) | 7 to 250 | 25 to 100 | 50% | 50% |
| Riboflavin | 5 to 400 | 50 to 100 | 50% | 50% |
| Folic acid | 0.100 to 5.0 | 0.200 to 0.400 | 100% | |
| Cyano-cobalamin (B12) | 0.001 to 0.008 | 0.003 to 0.005 | 100% | |
| Pyridoxine | 1.0 to 100 | 2.0 to 15 | 100% | |
| B Magnesium ($Mg^{2+}$) | 50 to 500 | 155 to 310 | 40% | 60% |
| Taurine | 75 to 2500 | 250 to 1000 | 70% | 30% |
| C D,alpha-Tocopherol | 15 to 1000 | 300 to 600 | 100% | |
| Ascorbate | 30 to 3000 | 300 to 600 | 50% | 50% |
| Ubiquinone | 5 to 200 | 30 to 60 | 50% | 50% |
| Quercetin | 10 to 250 | 75 to 150 | 100% | |
| Copper ($Cu^{2+}$) | 0.5 to 3.0 | 1.0 to 2.0 | 75% | 25% |
| Zinc ($Zn^{2+}$) | 2 to 50 | 5 to 10 | 25% | 75% |
| Selenium | 0.05 to 0.20 | 0.10 to 0.2 | 100% | |
| D Chromium | 0.008 to 0.63 | 0.025 to 0.25 | 100% | |
| Vanadium | 7.5 to 375 | 25 to 150 | 100% | |
| α-Lipoic Acid | 90 to 1500 | 300 to 600 | 50% | 50% |
| Nicotinamide | 3 to 375 | 10 to 150 | 25% | 75% |
| Melatonin | 0.05 to 10 | 0.25 to 5.0 | 40% | 60% |

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquids, emulsions, tablets, transmembrane delivery systems, electrophoretic delivery systems and capsules.

The dosage forms of this invention can be formulated for administration at rates of two or more unit dosage forms per day. Tableted unit dosage forms to be taken three to four times per day are preferred.

The following examples are offered for purposes of illustration only.

EXAMPLE I

A single layer tablet, substantially homogenous in composition, which will disintegrate upon ingestion to provide simultaneous accessibility to all components, is prepared with the following composition:

TABLE III

FOR RELEASE IN THE STOMACH

| | | % of formula |
|---|---|---|
| $Mg(C_6H_{13}N_4O_2)_2$ | Magnesium L-Arginate | 15.21% |
| $Mg(C_6H_7O_6)_2$ | Magnesium L-Ascorbate | 15.20% |
| $Mg(C_5H_9NO_3S)_2$ | Magnesium L-acetyl-Cysteine | 3.82% |
| $C_8H_{12}O_2S_2$ | Magnesium alpha-Lipoate | 4.14% |
| $(C_2H_7NO_3S)_2Mg$ | Magnesium Taurate | 4.87% |
| MgO | Magnesium Oxide | 11.01% |
| $(C_2H_7NO_3S)_2Zn$ | Zinc Taurate | 0.90% |
| $C_{35}H_{53}NO_3$ | D α-Tocopherol Nicotinate | 17.75% |
| $C_{19}H_{19}N_7O_6$ | Folic acid | 0.011% |
| $C_5H_{11}NO_2Se$ | L-Selenomethionine | 0.004% |

TABLE III-continued

FOR RELEASE IN THE STOMACH

| | | % of formula |
|---|---|---|
| $C_{17}H_{20}N_4O_6$ | Riboflavin | 0.36% |
| $C_8H_{12}N_2O_2$ | Pyridoxamine | 0.21% |
| | Excipients | |
| $Mg(C_{18}H_{35}O_2)_2$ | Magnesium Stearate | 0.78% |
| — | Starch | 25.75% |

Methods of Administration and Types of Utility

The compositions and dosage forms of the invention are useful for treating chronic glaucoma. The carefully chosen active ingredients of the invention act in a well-defined and complementary biochemical partnership to ensure that vascular risk factors are reduced in chronic glaucoma patients. The resulting improvement in systemic and ocular vascular health, especially in vascular endothelial health, maximizes the potential for success of current glaucoma therapeutics and minimizes the potential that present treatment regimes, concentrating as they do upon IOP reduction, will fail because of neglected, unrecognized or unappreciated ocular vascular inadequacy. The age group most commonly first diagnosed with glaucoma also is the age group moving into the physiological arena of reduced cellular efficiency secondary to age; at the same time it faces a concomitant increasing incidence of generalized vascular disability and associated chronic disease (e.g., diabetes mellitus, hypertension, hyperlipidosis, hyperinsulinemia). Many of the latter pathologies are associated with progressively widespread and worsening vascular health, a situation that imposes additional serious risk factors for glaucoma patients.

By positively influencing the NO/ET-1 balance, reducing adverse homocysteine effects, modulating a controlled reduction in $Ca^{+2}$ cellular inflow via physiological calcium channel blockade, reducing platelet aggregation, lowering microviscosity and improving laminar flow, reducing the inflammatory risks associated with local free radicals such as hydroxyls and limiting the rate the oxidation of low density lipids, the invention provides significant protection for glaucoma patients whether or not the measured IOP is high, normal or low. In performing this task, it reduces the risk of progressive visual field loss and eventual optic nerve atrophy commonly associated with chronic glaucoma.

Epidemiological studies have confirmed repeatedly that inadequate dietary intake of $Mg^{+2}$, ascorbate and folic acid, among others, is common in the general public and is especially rampant in alcoholics, institutionalized patients, cigarette smokers and the elderly. Other patients have disturbances of reduced absorption or abnormal loss of these and other critical biofactors (e.g., hypochlorhydria, diabetes mellitus, hyperinsulinemia, renal pathology, small or large bowel pathology, etc.) Another subset of patients suffers from a variety of primary diseases that create an underlying foundation of vascular dysfunction which is worsened by coexistent deficiencies (e.g., essential hypertension, congenital dyslipogenesis, aging, diabetes mellitus type 1 or type 2, etc.) The distribution of chronic glaucoma patients among any of these groups is no less than in the general public. The invention is especially useful in reducing the risk of harm associated with the vasculopathy of these conditions. While it should be expected that an improvement in vascular health will be generally beneficial to all of these clinical groups, this invention focuses upon the reduction in risk for the chronic glaucoma patient, regardless of IOP levels, who is inherently so much at risk of vascular-induced visual loss and blindness.

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

We claim:

1. A unit dosage form for the treatment of chronic glaucomas, comprising therapeutically effective amounts of:
   (a) a cyclic GMP increasing agent comprising folic acid,
   (b) an intracellular calcium signal modulation agent comprising magnesium,
   (c) a cell membrane integrity maintenance agent comprising D,α-tocopherol and ascorbate, and
   (d) a hyperinsulinemia modulating agent comprising α-lipoic acid.

2. A unit dosage form in accordance with claim 1 in which:
   (a) said cyclic GMP increasing agent further comprises L-arginine and N-acetyl-cysteine,
   (b) said intracellular calcium signal modulation agent further comprises taurine,
   (c) said cell membrane integrity maintenance agent further comprises selenium, and
   (d) said hyperinsulinemia modulation agent further comprises nicotinamide.

3. A unit dosage form in accordance with claim 2 in which said agents are present in the following approximate amounts in milligrams:

| | |
|---|---|
| L-arginine | 100 to 4500 |
| N-acetyl-cysteine | 75 to 2500 |
| folic acid | 0.100 to 5.0 |
| magnesium | 50 to 500 |
| taurine | 75 to 2500 |
| D,α-tocopherol | 15 to 1000 |
| ascorbate | 30 to 5000 |
| selenium | 0.05 to 0.20 |
| α-lipoic acid | 90 to 1500 |
| nicotinamide | 3 to 375 |

4. A unit dosage form in accordance with claim 3 in which said unit dosage form is a bilayer tablet comprising an immediate-release layer and a sustained-release layer, and said agents are distributed between said immediate-release layer and said sustained-release layer in the following approximate proportions expressed as weight percents:

| | Immediate-Release | Sustained-Release |
|---|---|---|
| L-arginine | 75% | 25% |
| N-acetyl-cysteine | 75% | 25% |
| folic acid | 100% | |
| magnesium | 40% | 60% |
| taurine | 70% | 30% |
| D,α-tocopherol | 100% | |
| ascorbate | 50% | 50% |
| selenium | 100% | |
| α-lipoic acid | 50% | 50% |
| nicotinamide | 25% | 75%. |

5. A unit dosage form in accordance with claim 2 in which said cyclic GMP increasing agent further comprises ginkgolides in an amount ranging from about 7 mg to about 250 mg.

6. A unit dosage form in accordance with claim 2 in which said cyclic GMP increasing agent further comprises riboflavin in an amount ranging from about 5 mg to about 400 mg, cyanocobalamine in an amount ranging from about 0.001 mg to about 0.008 mg, and pyridoxine in an amount ranging from about 1 mg to about 100 mg.

7. A unit dosage form in accordance with claim 2 in which said cyclic GMP increasing agent further comprises ginkgolides in an amount ranging from about 7 mg to about 250 mg, riboflavin in an amount ranging from about 5 mg to about 400 mg, cyanocobalamin in an amount ranging from about 0.0001 mg to about 0.0008 mg, and pyridoxine in an amount ranging from about 1 mg to about 100 mg.

8. A unit dosage form in accordance with claim 7 in which said unit dosage form is a bilayer tablet comprising an immediate-release layer and a sustained-release layer, and said ginkgolides, said riboflavin, said cyanocobalamin and said pyridoxine are distributed between said immediate-release layer and said sustained-release layer in the following approximate proportions expressed as weight percents:

| | Immediate-Release | Sustained-Release |
|---|---|---|
| ginkgolides | 50% | 50% |
| riboflavin | 50% | 50% |
| cyanocobalamin | 100% | |
| pyridoxine | 100%. | |

9. A unit dosage form in accordance with claim 2 in which said cell membrane integrity maintenance agent further comprises $Cu^{2+}$ in an amount ranging from about 0.5 mg to about 3.0 mg.

10. A unit dosage form in accordance with claim 2 in which said cell membrane integrity maintenance agent further comprises $Zn^{2+}$ in an amount ranging from about 2 mg to about 50 mg.

11. A unit dosage form in accordance with claim 2 in which said cell membrane integrity maintenance agent further comprises $Cu^{2+}$ in an amount ranging from about 0.5 mg to about 3.0 mg, and $Zn^{2+}$ in an amount ranging from about 2 mg to about 50 mg.

12. A unit dosage form in accordance with claim 11 in which said unit dosage form is a bilayer tablet comprising an immediate-release layer and a sustained-release layer, and said $Cu^{+2}$ and said $Zn^{+2}$ are distributed between said immediate-release layer and said sustained-release layer in the following approximate proportions expressed as weight percents:

|  | Immediate-Release | Sustained-Release |
|---|---|---|
| $Cu^{+2}$ | 75% | 25% |
| $Zn^{+2}$ | 25% | 75%. |

13. A unit dosage form in accordance with claim 2 in which said cell membrane integrity maintenance agent further comprises ubiquinone in an amount ranging from about 5 mg to about 200 mg.

14. A unit dosage form in accordance with claim 2 in which said cell membrane integrity maintenance agent further comprises quercetin in an amount ranging from about 10 mg to about 250 mg.

15. A unit dosage form in accordance with claim 2 in which said cell membrane integrity maintenance agent further comprises $Cu^{2+}$ in an amount ranging from about 0.5 mg to about 3.0 mg, and $Zn^{2+}$ in an amount ranging from about 2 mg to about 50 mg, ubiquinone in an amount ranging from about 5 mg to about 200 mg, and quercetin in an amount ranging from about 10 mg to about 250 mg.

16. A unit dosage form in accordance with claim 15 in which said unit dosage form is a bilayer tablet comprising an immediate-release layer and a sustained-release layer, and said $Cu^{+2}$, said $Zn^{+2}$, said ubiquinone, and said quercetin are distributed between said immediate-release layer and said sustained-release layer in the following approximate proportions expressed as weight percents:

|  | Immediate-Release | Sustained-Release |
|---|---|---|
| $Cu^{+2}$ | 75% | 25% |
| $Zn^{+2}$ | 25% | 75% |
| ubiquinone | 50% | 50% |
| quercetin | 100%. |  |

17. A unit dosage form in accordance with claim 2 in which said hyperinsulinemia modulation agent further comprises chromium in an amount ranging from about 0.008 mg to about 0.063 mg.

18. A unit dosage form in accordance with claim 2 in which said hyperinsulinemia modulation agent further comprises vanadium in an amount ranging from about 7.5 mg to about 375 mg.

19. A unit dosage form in accordance with claim 2 in which said hyperinsulinemia modulation agent further comprises melatonin in an amount ranging from about 0.05 mg to about 10 mg.

20. A unit dosage form in accordance with claim 2 in which said hyperinsulinemia modulation agent further comprises chromium in an amount ranging from about 0.008 mg to about 0.063 mg and vanadium in an amount ranging from about 7.5 mg to about 375 mg.

21. A unit dosage form in accordance with claim 2 in which said hyperinsulinemia modulation agent further comprises chromium in an amount ranging from about 0.008 mg to about 0.063 mg, vanadium in an amount ranging from about 7.5 mg to about 375 mg, and melatonin in an amount ranging from about 0.05 mg to about 10 mg.

22. A unit dosage form in accordance with claim 21 in which said unit dosage form is a bilayer tablet comprising an immediate-release layer and a sustained-release layer, and said chromium, vanadium and melatonin are distributed between said immediate-release layer and said sustained-release layer in the following approximate proportions expressed as weight percents:

|  | Immediate-Release | Sustained-Release |
|---|---|---|
| chromium | 100% |  |
| vanadium | 100% | 100% |
| melatonin | 40% | 60%. |

23. A unit dosage form in accordance with claim 2 in which said cyclic GMP increasing agent further comprises ginkgolides in an amount ranging from about 7 mg to about 250 mg, riboflavin in an amount ranging from about 5 mg to about 400 mg, cyanocobalamine in an amount ranging from about 0.001 mg to about 0.008 mg, and pyridoxine in an amount ranging from about 1 mg to about 100 mg; said cell membrane integrity maintenance agent further comprises $Cu^{2+}$ in an amount ranging from about 0.5 mg to about 3.0 mg, and $Zn^{2+}$ in an amount ranging from about 2 mg to about 50 mg, ubiquinone in an amount ranging from about 5 mg to about 200 mg, and quercetin in an amount ranging from about 10 mg to about 250 mg; and said hyperinsulinemia modulation agent further comprises chromium in an amount ranging from about 0.008 mg to about 0.063 mg and vanadium in an amount ranging from about 7.5 mg to about 375 mg.

24. A unit dosage form in accordance with claim 2 in which said cyclic GMP increasing agent further comprises ginkgolides in an amount ranging from about 7 mg to about 250 mg, riboflavin in an amount ranging from about 5 mg to about 400 mg, cyanocobalamine in an amount ranging from about 0.001 mg to about 0.008 mg, and pyridoxine in an amount ranging from about 1 mg to about 100 mg; said cell membrane integrity maintenance agent further comprises $Cu^{2+}$ in an amount ranging from about 0.5 mg to about 3.0 mg, and $Zn^{2+}$ in an amount ranging from about 2 mg to about 50 mg, ubiquinone in an amount ranging from about 5 mg to about 200 mg, and quercetin in an amount ranging from about 10 mg to about 250 mg; and said hyperinsulinemia modulation agent further comprises chromium in an amount ranging from about 0.008 mg to about 0.063 mg, vanadium in an amount ranging from about 7.5 mg to about 375 mg, and melatonin in an amount ranging from about 0.05 mg to about 10 mg.

25. A unit dosage form in accordance with claim 1 in which said unit dosage form is an oral dosage form, and said D,α-tocopherol is in the form of D,α-tocopherol nicotinate and is present in an amount ranging from about 20 mg to about 1250 mg.

26. A unit dosage form in accordance with claim 1 in which said unit dosage form is an oral dosage form, and said magnesium is in the form of magnesium L-ascorbate and is present in an amount ranging from about 460 mg to about 5400 mg.

27. A unit dosage form in accordance with claim 1 in which said unit dosage form is an oral dosage form, and said magnesium is in the form of magnesium L-acetyl cysteinate and is present in an amount ranging from about 430 mg to about 2600 mg.

28. A unit dosage form in accordance with claim 1 in which said unit dosage form is an oral dosage form, and said magnesium is in the form of magnesium L-arginate and is present in an amount ranging from about 180 mg to about 4600 mg.

29. A unit dosage form in accordance with claim 1 in which said unit dosage form is an oral dosage form, and said magnesium is in the form of magnesium N-thioctylarginate and is present in an amount ranging from about 360 mg to about 7000 mg.

30. A unit dosage form in accordance with claim 1 in which said unit dosage form is an oral dosage form, and said magnesium is in the form of magnesium 2,N-thioctylcysteinate and is present in an amount ranging from about 360 mg to about 4000 mg.

31. A unit dosage form in accordance with claim 1 in which said unit dosage form is an oral dosage form, and said magnesium is in the form of magnesium 2,N-thioctyltaurate and is present in an amount ranging from about 250 mg to about 5000 mg.

32. A unit dosage form in accordance with claim 1 in which said unit dosage form is an oral dosage form, and said magnesium is in the form of magnesium acetate and is present in an amount ranging from about 430 mg to about 4600 mg.

33. A unit dosage form in accordance with claim 1 in which said unit dosage form is an oral dosage form, and said magnesium is in the form of magnesium α-lipoate and is present in an amount ranging from about 530 mg to about 1600 mg.

34. A unit dosage form in accordance with claim 1 in which said unit dosage form is an oral dosage form, and said magnesium is in the form of magnesium taurate and is present in an amount ranging from about 330 mg to about 3000 mg.

35. A unit dosage form in accordance with claim 1 in which said unit dosage form is an oral dosage form, and said magnesium is in the form of magnesium citrate and is present in an amount ranging from about 430 mg to about 4000 mg.

36. A unit dosage form in accordance with claim 1 in which said unit dosage form is an oral dosage form, and said magnesium is in the form of magnesium oxide and is present in an amount ranging from about 50 mg to about 850 mg.

37. A unit dosage form in accordance with claim 10 in which said unit dosage form is an oral dosage form and said $Zn^{+2}$ is in the form of zinc taurate and is present in an amount ranging from about 7 mg to about 250 mg.

38. A unit dosage form in accordance with claim 10 in which said unit dosage form is an oral dosage form and said $Zn^{+2}$ is in the form of zinc acetate and is present in an amount ranging from about 10 mg to about 350 mg.

39. A unit dosage form in accordance with claim 10 in which said unit dosage form is an oral dosage form and said $Zn^{+2}$ is in the form of zinc L-acetylcysteinate and is present in an amount ranging from about 10 mg to about 1000 mg.

40. A unit dosage form in accordance with claim 10 in which said unit dosage form is an oral dosage form and said $Zn^{+2}$ is in the form of zinc L-arginate and is present in an amount ranging from about 15 mg to about 1100 mg.

41. A unit dosage form in accordance with claim 10 in which said unit dosage form is an oral dosage form and said $Zn^{+2}$ is in the form of zinc α-lipoate and is present in an amount ranging from about 7 mg to about 230 mg.

42. A unit dosage form in accordance with claim 9 in which said unit dosage form is an oral dosage form and said $Cu^{+2}$ is in the form of copper L-arginate and is present in an amount ranging from about 2 mg to about 40 mg.

43. A unit dosage form in accordance with claim 9 in which said unit dosage form is an oral dosage form and said $Cu^{+2}$ is in the form of copper L-acetylcysteinate and is present in an amount ranging from about 2 mg to about 40 mg.

44. A unit dosage form in accordance with claim 2 in which at least one of said L-arginine and said taurine is in the form of a complex having the formula $$RMX$$

wherein:

R is a member selected from the group consisting of L-arginine, taurine, bis-L-arginine, and bis-taurine;

M is a member selected from the group consisting of $Mg^{+2}$, $Se^{+2}$, $Cu^{+2}$, and $Zn^{+2}$; and X is a member selected from the group consisting of hydroxide, halide, sulfate, acetate, ascorbate, and bis-ascorbate.

45. A unit dosage form in accordance with claim 2 in which said magnesium is in the form of a complex having the formula $$RMg^{+2}X$$

wherein:

R is a member selected from the group consisting of cysteine, acetylcysteine, N-acetylcysteine, mercaptopropionylglycine, and L-2-oxothiazolidine-4-carboxylate; and X is a member selected from the group consisting of hydroxide, halide, sulfate, phosphate, acetate, ascorbate, and bis-ascorbate.

46. A unit dosage form in accordance with claim 2 in which said cell membrane integrity maintenance agent further comprises $Cu^{+2}$, and said $Cu^{+2}$ is in the form of a complex having the formula $$RCu^{+2}X$$

wherein:

R is a member selected from the group consisting of cysteine, acetylcysteine, N-acetylcysteine, mercaptopropionylglycine, and L-2-oxothiazolidine-4-carboxylate; and X is a member selected from the group consisting of hydroxide, halide, sulfate, phosphate, acetate, ascorbate, and bis-ascorbate.

47. A unit dosage form in accordance with claim 2 in which said cell membrane integrity maintenance agent further comprises $Zn^{+2}$, and said $Zn^{+2}$ is in the form of a complex having the formula $$RZn^{+2}X$$

wherein:

R is a member selected from the group consisting of cysteine, acetylcysteine, N-acetylcysteine, mercaptopropionylglycine, and L-2-oxothiazolidine-4-carboxylate; and X is a member selected from the group consisting of hydroxide, halide, sulfate, phosphate, acetate, ascorbate, and bis-ascorbate.

48. A unit dosage form in accordance with claim 1 in which said α-lipoic acid is in the form of a complex having the formula $$RMX$$

wherein:

R is α-lipoic acid;

M is a member selected from the group consisting of Mg$^{+2}$, Cu$^{+2}$, Zn$^{+2}$, and Se$^{+2}$; and X is a member selected from the group consisting of hydroxide, halide, sulfate, phosphate, acetate, ascorbate, and bis-ascorbate.

49. A unit dosage form in accordance with claim 2 in which said cell membrane integrity maintenance agent further comprises Cu$^{+2}$ and Zn$^{+2}$, and at least one of said magnesium, selenium Cu$^{+2}$ and Zn$^{+2}$ is in the form of a complex having the formula $$R_nMX$$

wherein:

R is a member selected from the group consisting of 2,N-thioctylarginine, 2,N-thioctylcysteine, 2,N-thioctyllysine, and 2,N-thioctyltaurine;

n is 1 or 2;

M is a member selected from the group consisting of Mg$^{+2}$, Cu$^{+2}$, Zn$^{+2}$, and Se$^{+2}$; and X is a member selected from the group consisting of hydroxide, halide, sulfate, phosphate, acetate, ascorbate, and bis-ascorbate.

50. A unit dosage form in accordance with claim 1 in which said magnesium is in the form of a member selected from the group consisting of magnesium hydroxide, magnesium halide, magnesium sulfate, magnesium phosphate, magnesium acetate, magnesium taurate, magnesium ascorbate, and magnesium bis-ascorbate.

51. A unit dosage form in accordance with claim 2 in which said selenium is in the form of a member selected from the group consisting of selenium hydroxide, selenium halide, selenium sulfate, selenium phosphate, selenium acetate, selenium ascorbate, selenium bis-ascorbate, selenomethionine, and yeast-derived selenium.

52. A unit dosage form in accordance with claim 9 in which said Cu$^{2+}$ is in the form of a member selected from the group consisting of cupric hydroxide, cupric halide, cupric sulfate, cupric phosphate, cupric acetate, cupric ascorbate, and cupric bis-ascorbate.

53. A unit dosage form in accordance with claim 10 in which said Zn$^{2+}$ is in the form of a member selected from the group consisting of zinc hydroxide, zinc halide, zinc sulfate, zinc phosphate, zinc acetate, zinc ascorbate, and zinc bis-ascorbate.

54. A unit dosage form in accordance with claim 18 in which said vanadium is in the form of a member selected from the group consisting of vanadium sulfate salts and bis(maltolato)oxovanadium(IV).

55. A unit dosage form in accordance with claim 17 in which said chromium is in the form of a member selected from the group consisting of chromium tripicolinate and chromium dinicotinate.

56. A unit dosage form in accordance with claim 1 in which said D,α-tocopherol is present in the form of a member selected from the group consisting of D,α-tocopherol succinate, D,α-tocopherol nicotinate, and D,α-tocopherol acetate.

* * * * *